United States Patent
Yaguchi

(10) Patent No.: US 12,396,627 B2
(45) Date of Patent: Aug. 26, 2025

(54) METHOD FOR CONTROLLING AIR FEEDING DEVICE AND AIR FEEDING DEVICE

(71) Applicant: OLYMPUS CORPORATION, Tokyo (JP)

(72) Inventor: Yoshitomo Yaguchi, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 852 days.

(21) Appl. No.: 17/475,652

(22) Filed: Sep. 15, 2021

(65) Prior Publication Data

US 2022/0000347 A1    Jan. 6, 2022

Related U.S. Application Data

(63) Continuation of application No. PCT/JP2019/013826, filed on Mar. 28, 2019.

(51) Int. Cl.
| | |
|---|---|
| A61L 2/00 | (2006.01) |
| A61B 1/00 | (2006.01) |
| A61B 1/015 | (2006.01) |
| A61M 39/22 | (2006.01) |

(52) U.S. Cl.
CPC .......... *A61B 1/015* (2013.01); *A61B 1/00068* (2013.01); *A61B 1/00121* (2013.01); *A61M 39/22* (2013.01); *A61M 2205/3355* (2013.01)

(58) Field of Classification Search
CPC . A61L 2/0082; A61L 2/18; A61L 2/20; A61L 2/24; A61B 1/00068; A61B 1/00006; A61B 1/12

USPC .......................................... 422/292, 300–301
See application file for complete search history.

(56) References Cited

U.S. PATENT DOCUMENTS

2017/0172399 A1    6/2017   Takada

FOREIGN PATENT DOCUMENTS

| EP | 3 175 775 A1 | 6/2017 |
|---|---|---|
| JP | 04-016169 B2 | 3/1992 |
| JP | H07-299031 A | 11/1995 |
| JP | 2009-142490 A | 7/2009 |
| JP | 2014-079369 A | 5/2014 |

(Continued)

OTHER PUBLICATIONS

International Search Report dated Jun. 18, 2019received in PCT/JP2019/013826.

*Primary Examiner* — Monzer R Chorbaji
(74) *Attorney, Agent, or Firm* — Scully, Scott, Murphy & Presser, P.C.

(57) ABSTRACT

An air feeding device includes: an endoscope connector connected to an endoscope conduit; a compressor connector connected to a compressor which discharges a gas; an air feeding conduit having one end connected to the endoscope connector, and another end connected to the compressor connector, an opening and closing valve disposed in the air feeding conduit; an atmosphere release valve connected to the air feeding conduit at a position between the other end and the opening and closing valve, the atmosphere release valve being capable of adjusting an atmosphere release rate of the gas from the air feeding conduit; a sensor configured to detect an internal pressure in the air feeding conduit; and a processor connected to the opening and closing valve, the atmosphere release valve, and the sensor.

19 Claims, 10 Drawing Sheets

(56) References Cited

FOREIGN PATENT DOCUMENTS

| | | | |
|---|---|---|---|
| JP | 5642907 | B1 | 12/2014 |
| JP | 5869702 | B2 | 2/2016 |
| JP | 3 175 775 | A1 * | 7/2017 ............... A61B 1/12 |
| WO | 2014/103881 | A1 | 7/2014 |
| WO | 2017/026138 | A1 | 2/2017 |
| WO | 2017/033483 | A1 | 3/2017 |

* cited by examiner

METHOD FOR CONTROLLING AIR FEEDING DEVICE AND AIR FEEDING DEVICE

CROSS REFERENCE TO RELATED APPLICATION

This application is a continuation application of PCT/JP2019/013826 filed on Mar. 28, 2019, the entire contents of which are incorporated herein by this reference.

BACKGROUND OF THE INVENTION

1. Field of the Invention

The present invention relates to a method for controlling an air feeding device which feeds a gas ejected from a compressor into an endoscope conduit, and to an air feeding device.

2. Description of the Related Art

Some endoscopes used in the medical field adopt a mode where the endoscope includes a conduit. A gas at a pressure higher than atmospheric pressure which is ejected from a compressor may be fed into the conduit of the endoscope.

For example, Japanese Patent No. 5642907 discloses an endoscope cleaning/disinfecting apparatus having a configuration where a gas is fed into a conduit of an endoscope. The gas fed into the conduit of the endoscope by the endoscope cleaning/disinfecting apparatus is used to drain liquid or the like in the conduit to the outside of the conduit.

For example, Japanese Patent No. 1737816 discloses an endoscope apparatus which feeds a gas to be ejected from a nozzle, provided at a distal end of an insertion portion of an endoscope, into a conduit of the endoscope. The gas fed into the conduit of the endoscope by the endoscope apparatus is used to drain an observation window.

In the device disclosed in Japanese Patent No. 5642907 or Japanese Patent No. 1737816, it is preferable that a pressure of a gas fed into the conduit of the endoscope fall within a predetermined range.

SUMMARY OF THE INVENTION

One aspect of the present invention is directed to a method for controlling an air feeding device which includes an endoscope connector connected to an endoscope conduit, a compressor connector connected to a compressor which discharges a gas, an air feeding conduit having one end connected to the endoscope connector, and another end connected to the compressor connector, an opening and closing valve disposed in the air feeding conduit, an atmosphere release valve connected to the air feeding conduit at a position between the other end and the opening and closing valve, the atmosphere release valve being capable of adjusting an atmosphere release rate of the gas from the air feeding conduit, and a sensor configured to detect an internal pressure in the air feeding conduit, the method including: introducing the gas from the compressor into the air feeding conduit and detecting the internal pressure in the air feeding conduit by the sensor in a state where the opening and closing valve is closed; adjusting the atmosphere release rate of the gas from the atmosphere release valve such that the internal pressure in the air feeding conduit falls within a predetermined reference range; closing the opening and closing valve and introducing the gas from the compressor into the air feeding conduit in a state where the atmosphere release rate of the atmosphere release valve is maintained and the atmosphere release rate is adjusted such that the internal pressure in the air feeding conduit falls within the predetermined reference range; and discharging the gas in the air feeding conduit from the endoscope connector by opening the opening and closing valve in a state where the gas is introduced from the compressor into the air feeding conduit and the internal pressure in the air feeding conduit falls within a predetermined range.

Another aspect of the present invention is directed to an air feeding device including: an endoscope connector connected to an endoscope conduit; a compressor connector connected to a compressor which discharges a gas; an air feeding conduit having one end connected to the endoscope connector, and another end connected to the compressor connector; an opening and closing valve disposed in the air feeding conduit; an atmosphere release valve connected to the air feeding conduit at a position between the other end and the opening and closing valve, the atmosphere release valve being capable of adjusting an atmosphere release rate of the gas from the air feeding conduit; a sensor configured to detect an internal pressure in the air feeding conduit; and a processor connected to the opening and closing valve, the atmosphere release valve, and the sensor, wherein the processor introduces the gas from the compressor into the air feeding conduit and detects the internal pressure in the air feeding conduit by the sensor in a state where the opening and closing valve is closed, adjusts the atmosphere release rate of the gas from the atmosphere release valve such that the internal pressure in the air feeding conduit falls within a predetermined reference range, closes the opening and closing valve and introduces the gas from the compressor into the air feeding conduit in a state where the atmosphere release rate of the atmosphere release valve is maintained and the atmosphere release rate is adjusted such that the internal pressure in the air feeding conduit falls within the predetermined reference range, and discharges the gas in the air feeding conduit from the endoscope connector by opening the opening and closing valve in a state where the gas is introduced from the compressor into the air feeding conduit and the internal pressure in the air feeding conduit falls within a predetermined range.

DETAILED DESCRIPTION OF THE PREFERRED EMBODIMENTS

Figure 1:
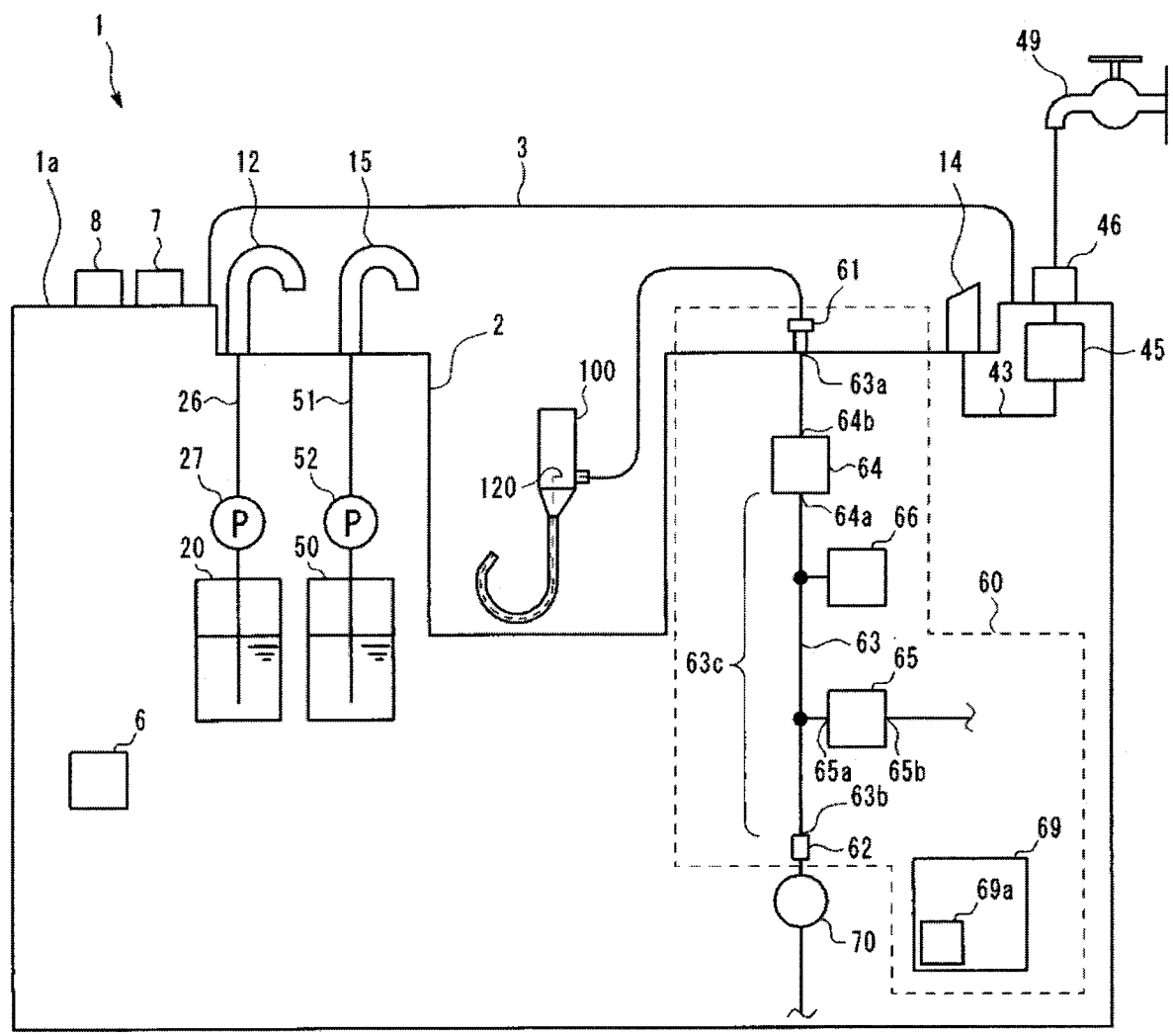
FIG. 1 is a view showing configurations of an endoscope reprocessor and an air feeding device of a first embodiment.

Hereinafter, preferred modes of the present invention will be described with reference to drawings. Note that in respective drawings used in the description made hereinafter, to allow respective constituent elements to have sizes which are visible in the drawings, each constituent element has a different scale, and the present invention is not limited to the number of constituent elements, the shape of the constituent elements, size ratios of the constituent elements, or relative positional relationships between the respective constituent elements described in these drawings.

First Embodiment

An air feeding device 60 of the present embodiment is a device which feeds a gas into an endoscope conduit 120 of an endoscope 100. As shown in FIG. 1, in the present embodiment, the air feeding device 60 is included in an endoscope reprocessor 1, for example. The endoscope reprocessor 1 is a device which performs reprocessing on at least one of an endoscope or an endoscopic accessory.

The reprocessing described in the present embodiment is not particularly limited, and may be any one of a rinsing treatment with water, a cleaning treatment which removes contamination such as organic substances, a disinfection treatment which neutralizes a predetermined microorganism, a sterilizing treatment which eliminates or kills all microorganisms, or a combination of these treatments.

Note that a mode of the air feeding device 60 is not limited to the mode where the air feeding device 60 is included in the endoscope reprocessor 1. For example, the air feeding device 60 may adopt a mode where the air feeding device 60 is included in a dryer which dries the endoscope 100. Alternatively, for example, the air feeding device 60 may adopt a mode where the air feeding device 60 feeds a gas which is to be sent from a distal end portion of an insertion portion of the endoscope 100 during the use of the endoscope 100.

The endoscope reprocessor 1 includes a controller 69, a power supply unit 6, a treatment tank 2, a compressor 70, and the air feeding device 60.

The controller 69 includes a processor, a memory, an input/output device, a power control device, and the like. The controller 69 is configured to execute a predetermined program according to instructions from a user to control actions of respective portions forming the endoscope reprocessor 1. For example, a function of each unit of the processor may be achieved by individual hardware. Alternatively, some of the respective units may be achieved by integral hardware. For example, the processor includes hardware, and the hardware may include at least either one of a circuit which performs processing on a digital signal or a circuit which performs processing on an analog signal. For the processor, any of various processors may be used, such as a CPU (central processing unit) or a DSP (digital signal processor). The processor may also be a hardware circuit using an ASIC (application specific integrated circuit) or an FPGA (field programmable gate array). In the description made hereinafter, the actions of respective components included in the endoscope reprocessor 1 and the air feeding device 60 are controlled by the controller 69 even in cases where no particular description is made.

The controller 69 forms the air feeding device 60, which will be described later. The controller 69 includes a memory 69a, such as a flash memory, which stores information on the adjustment state of an atmosphere release valve 65, which will be described later.

An operation portion 7 and a display unit 8 form a user interface which transmits and receives information between the controller 69 and a user. The operation portion 7 includes an operation member, such as a push switch or a touch sensor, which accepts action instructions from the user. The action instruction from the user is converted to an electric signal by the operation portion 7, and is inputted into the controller 69. The action instruction from the user may be an instruction to start the reprocessing, for example.

The display unit 8 includes, for example, a display device which displays images or letters, a light emitting device which emits light, a speaker which emits sounds, a vibrator which generates vibrations, or the combination of the devices. The display unit 8 outputs information to the user from the controller 69.

A mode may be adopted where a part of or the whole of the operation portion 7 and the display unit 8 is included in electronic equipment which is separated from a body portion 1a of the endoscope reprocessor 1, the electronic equipment performing wired communication or wireless communication with the controller 69.

The power supply unit 6 supplies power to respective components of the endoscope reprocessor 1. The power supply unit 6 distributes power obtained from the outside, such as a commercial power supply, to the respective components. The power supply unit 6 may include a power generation device or a battery.

The treatment tank 2 has a recessed shape having an opening portion, and can store liquid. One or a plurality of endoscopes 100 can be disposed in the treatment tank 2.

In the description made hereinafter, upward indicates a position farther from the ground surface than a comparison object, and downward indicates a position closer to the ground surface than the comparison object. In the description made hereinafter, high and low indicates a height relationship in the direction of gravity.

A lid 3 is provided to an upper portion of the treatment tank 2, and the lid 3 opens/closes the opening portion of the treatment tank 2. In the case where the reprocessing is performed on the endoscope 100 in the treatment tank 2, the opening portion of the treatment tank 2 is closed by the lid 3. The lid 3 has an opening portion provided with a filter. Even in a state where the treatment tank 2 is closed by the lid 3, air pressure in the treatment tank 2 is substantially equivalent to atmospheric pressure.

The treatment tank 2 is provided with a cleaning solution nozzle 15, a medicinal solution nozzle 12, a water nozzle 14, and an endoscope connection portion 61. Although not shown in the drawing, the treatment tank 2 has a drain port for draining liquid present in the treatment tank 2.

The cleaning solution nozzle 15 is an opening portion communicating with a cleaning solution tank 50 via a cleaning solution conduit 51, the cleaning solution tank 50 storing cleaning solution. The cleaning solution is used for cleaning treatment. A cleaning solution pump 52 is provided to the cleaning solution conduit 51. The cleaning solution pump 52 is connected to the controller 69, and the action of the cleaning solution pump 52 is controlled by the controller 69. When the cleaning solution pump 52 is operated, the cleaning solution in the cleaning solution tank 50 is transferred into the treatment tank 2.

The medicinal solution nozzle 12 is an opening portion communicating with a medicinal solution tank 20 via a medicinal solution conduit 26. The medicinal solution tank 20 stores medicinal solution. The kind of medicinal solution stored in the medicinal solution tank 20 is not particularly limited. However, in the present embodiment, an example of the medicinal solution may be disinfecting liquid used for disinfection treatment, or sterilizing liquid used for sterilizing treatment. An example of the disinfecting liquid or the sterilizing liquid may be peracetic acid aqueous solution.

A medicinal solution pump 27 is provided to the medicinal solution conduit 26. When the medicinal solution pump 27 is operated, the medicinal solution in the medicinal solution tank 20 is transferred into the treatment tank 2 via the medicinal solution conduit 26 and the medicinal solution nozzle 12.

The water nozzle 14 is a conduit communicating with a water supply source connection portion 46 via a water supply conduit 43. The water supply source connection portion 46 is connected, via a hose or the like, to a water supply source 49, such as water supply equipment, which sends water.

A water introduction valve 45 is provided to the water supply conduit 43. The water introduction valve 45 is connected to the controller 69, and the action of the water introduction valve 45 is controlled by the controller 69. When the water introduction valve 45 is brought into an open state, water supplied from the water supply source 49 is introduced into the treatment tank 2.

The endoscope connection portion 61 forms the air feeding device 60, which will be described later. The endoscope connection portion 61, which forms an endoscope connector, is connected to the endoscope conduit 120 of the endoscope 100 disposed in the treatment tank 2. The endoscope connection portion 61 may be directly connected to the endoscope conduit 120, or may be connected to the endoscope conduit 120 via a tube or the like.

The compressor 70 ejects a gas at a pressure higher than atmospheric pressure. The kind of gas ejected from the compressor 70 is not particularly limited. However, in the present embodiment, the compressor 70 compresses and ejects air. The compressor 70 is electrically connected to the controller 69, and the action of the compressor 70 is controlled by the controller 69.

The air feeding device 60 includes an air feeding conduit 63, the endoscope connection portion 61, a compressor connection portion 62, an opening and closing valve 64, the atmosphere release valve 65, a sensor 66, and the controller 69. The air feeding device 60 performs air feeding processing of feeding gas, which is introduced from the compressor 70, into the endoscope conduit 120.

The air feeding conduit 63 is a hollow conduit which is open at both one end 63a, being a first end, and the other end 63b, being a second end. The one end 63a of the air feeding conduit 63 is connected to the endoscope connection portion 61. The other end 63b of the air feeding conduit 63 is connected to the compressor connection portion 62.

As described above, the endoscope conduit 120 of the endoscope 100 can be connected to the endoscope connection portion 61. In the case where the endoscope conduit 120 is connected to the endoscope connection portion 61, the one end 63a of the air feeding conduit 63 and the endoscope conduit 120 communicate with each other.

The compressor connection portion 62 forming a compressor connector is connected to the compressor 70. The other end 63b of the air feeding conduit 63 communicates with the compressor 70 via the compressor connection portion 62. In other words, a gas ejected from the compressor 70 is introduced into the air feeding conduit 63 through the compressor connection portion 62.

The opening and closing valve 64 is provided to the air feeding conduit 63. The opening and closing valve 64 is a so-called two-port solenoid valve which has two ports, that is, a first port 64a and a second port 64b. The first port 64a communicates with the other end 63b side of the air feeding conduit 63. The second port 64b communicates with the one end 63a side of the air feeding conduit 63.

The opening and closing valve 64 is electrically connected to the controller 69, and the action of the opening and closing valve 64 is controlled by the controller 69. When the opening and closing valve 64 is in an open state, a flow passage between the first port 64a and the second port 64b is released, so that fluid is allowed to flow from the first port 64a to the second port 64b. When the opening and closing valve 64 is in a closed state, the flow passage between the first port 64a and the second port 64b is blocked.

The atmosphere release valve 65 is connected to a first section 63c. The first section 63c is a section of the air feeding conduit 63 which is disposed between the other end 63b and the opening and closing valve 64. The atmosphere release valve 65 can adjust an atmosphere release rate of a gas from the inside of the first section 63c of the air feeding conduit 63. The atmosphere release valve 65 is electrically connected to the controller 69, and the action of the atmosphere release valve 65 is controlled by the controller 69.

More specifically, the atmosphere release valve 65 has an input port 65a and an output port 65b. The input port 65a communicates with the first section 63c of the air feeding conduit 63. From the output port 65b, gas or liquid is released to the atmosphere. Neither the number of input ports 65a nor the number of output ports 65b is limited, and the number of input ports 65a and the number of output ports 65b may be one or plural.

Note that the output port 65b is not limited to a mode where gas or liquid is directly released from the output port 65b to the atmosphere. The output port 65b may adopt a mode where the output port 65b is connected to the inside of a container with an internal pressure substantially equivalent to atmospheric pressure, and gas or liquid is released from the output port 65b to the atmosphere via the container. The container forms a device which captures liquid present in fluid ejected from the output port 65b, for example. The output port 65b may be provided with a filter or a silencer.

The atmosphere release valve 65 adjusts the "atmosphere release rate" of a gas from the inside of the first section 63c of the air feeding conduit 63. Specifically, the "atmosphere release rate" indicates the flow rate of gas ejected from the inside of the first section 63c to the outside of the first section 63c via the atmosphere release valve 65, when the internal pressure (air pressure) in the first section 63c is higher than atmospheric pressure. The flow rate is expressed by a volume of gas ejected from the inside of the first section 63c to the outside of the first section 63c per predetermined unit time period. In other words, the atmosphere release valve 65 has a configuration of changing (adjusting) the flow rate of gas flowing from the input port 65a to the output port 65b.

Note that the range of adjustment of the atmosphere release rate performed by the atmosphere release valve 65 may include a case where the flow rate of gas ejected from the inside of the first section 63c to the outside of the first section 63c is zero. In other words, the atmosphere release valve 65 may have a configuration which blocks the flow passage between the input port 65a and the output port 65b.

The specific configuration of the atmosphere release valve 65 which adjusts the atmosphere release rate is not particularly limited. In the present embodiment, for example, the atmosphere release valve 65 has a configuration of adjusting an atmosphere release rate by changing the cross-sectional area of the flow passage between the input port 65a and the output port 65b. To be more specific, the atmosphere release valve 65 in the present embodiment includes a plurality of two-port solenoid valves each having a predetermined cross-sectional area of a flow passage. One port of each of the plurality of solenoid valves communicates with the input port 65a, and the other port of each of the plurality of solenoid valves is connected to the output port 65b.

The atmosphere release valve 65 in the present embodiment having such a configuration changes the cross-sectional area of the flow passage between the input port 65a and the output port 65b by changing the number of solenoid valves which are brought into an open state. The atmosphere release valve 65 in the present embodiment is formed of a simple two-port solenoid valve, thus enabling low cost. Further, the atmosphere release valve 65 can be easily controlled.

The atmosphere release valve 65 may adopt a mode having a mechanism which continuously changes the cross-sectional area of a flow passage between the input port 65a and the output port 65b. The atmosphere release valve 65 may also have a mode where the atmosphere release valve 65 includes a solenoid valve which opens/closes the flow passage between the input port 65a and the output port 65b, and the atmosphere release valve 65 adjusts the atmosphere release rate by changing the ratio (duty ratio) of the time period during which the solenoid valve is brought into a closed state to the time period during which the solenoid valve is brought into an open state per predetermined unit time period.

The sensor 66 is a pressure sensor which detects the internal pressure in the first section 63c of the air feeding conduit 63. The sensor 66 is electrically connected to the controller 69. In FIG. 1, for example, the sensor 66 is disposed between the opening and closing valve 64 and the atmosphere release valve 65 in the first section 63c of the air feeding conduit 63. However, the sensor 66 may be disposed between the atmosphere release valve 65 and the other end 63b in the first section 63c.

Although not shown in the drawing, the first section 63c of the air feeding conduit 63 may be provided with a filter which filters a gas.

Figure 2:
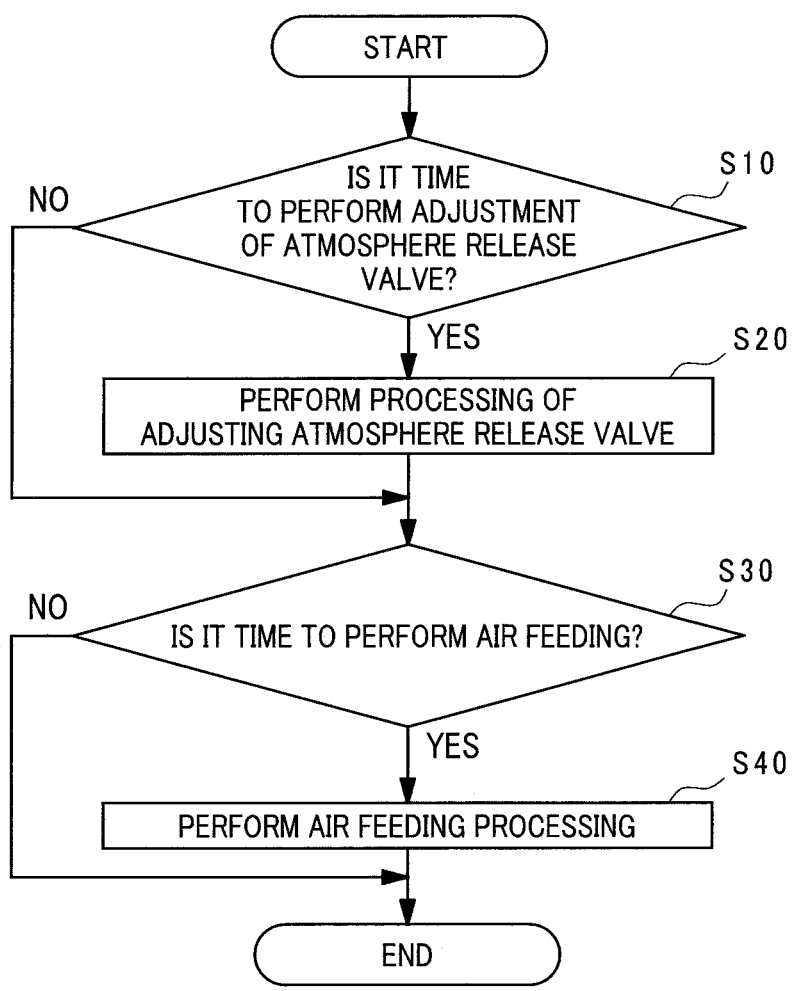
FIG. 2 is a flowchart showing an action of a control unit in the first embodiment.
Figure 3:
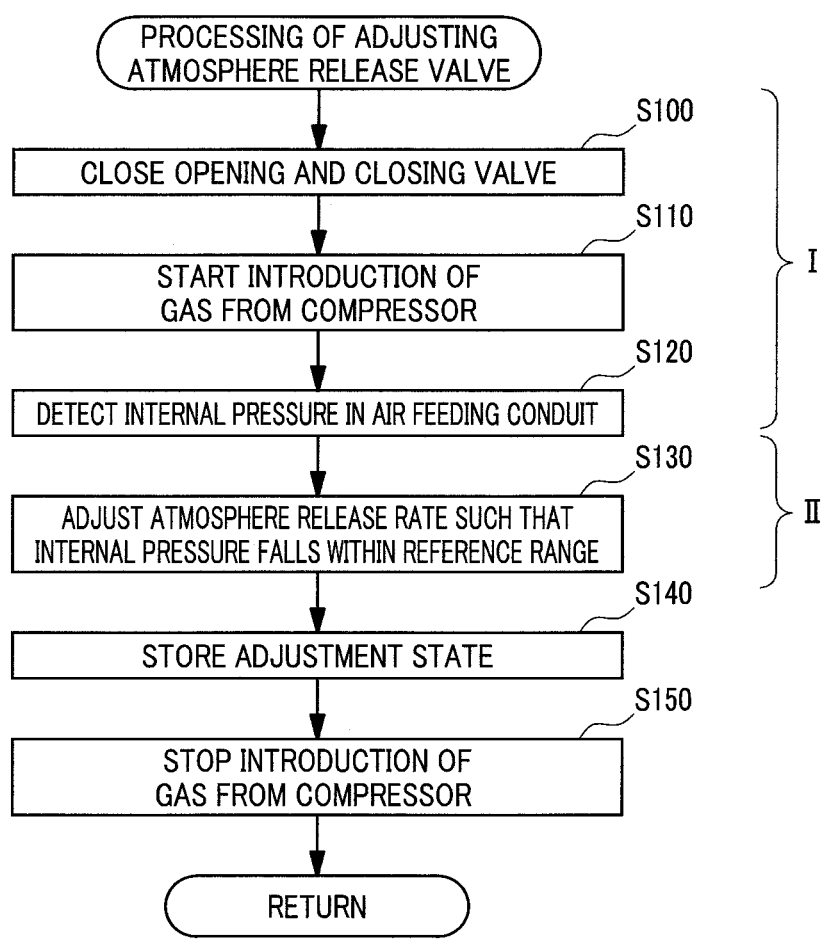
FIG. 3 is a flowchart of processing of adjusting an atmosphere release valve in the first embodiment.
Figure 4:
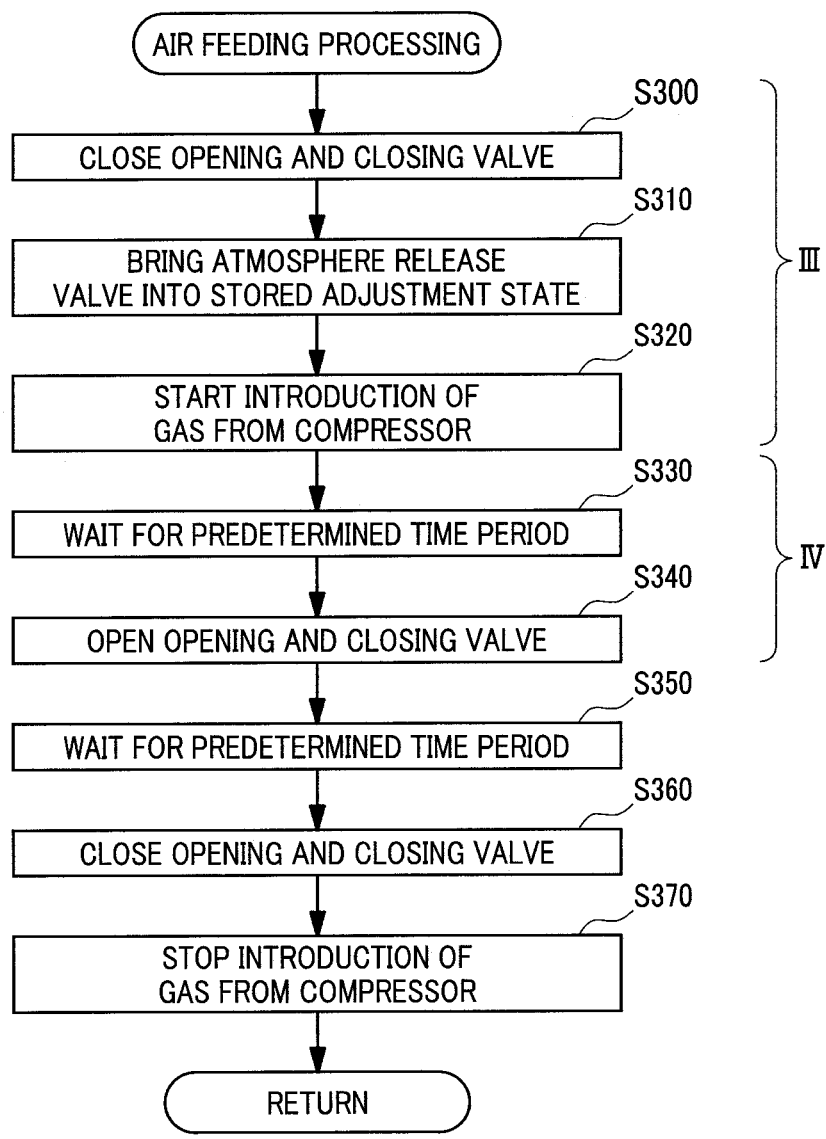
FIG. 4 is a flowchart of air feeding processing in the first embodiment.

The controller 69 controls the action of the air feeding device 60 having the above-mentioned configuration. FIG. 2, FIG. 3, and FIG. 4 are flowcharts showing a method for controlling the air feeding device 60.

When the air feeding device 60 (the endoscope reprocessor 1) is turned on, the controller 69 performs processing shown in FIG. 2 repeatedly in a predetermined cycle. As shown in FIG. 2, in step S10, the controller 69 determines whether it is time to perform adjustment of the atmosphere release valve 65.

When the controller 69 determines in step S10 that it is time to perform adjustment of the atmosphere release valve 65, the processing advances to step S20 in which processing of adjusting the atmosphere release valve 65 is performed and, thereafter, the processing advances to step S30. When the controller 69 determines in step S10 that it is not time to perform adjustment of the atmosphere release valve 65, the processing skips step S20 and advances to step S30.

In step S10, a determination reference for whether it is time to perform adjustment of the atmosphere release valve 65 is not particularly limited.

In the present embodiment, for example, in the case where step S10 is performed for the first time after the air feeding device 60 (the endoscope reprocessor 1) is turned on, the controller 69 determines that it is time to perform adjustment of the atmosphere release valve 65. In the case where step S10 is performed for the second or subsequent time, the controller 69 determines that it is not time to perform adjustment of the atmosphere release valve 65. Further, in the case where the first air feeding processing for that day is not yet performed, the controller 69 in the present embodiment determines in step S10 that it is time to perform adjustment of the atmosphere release valve 65.

For example, the memory 69a stores the date and time at which the adjustment of the atmosphere release valve 65 is performed in the past. When the elapsed time period from the stored date and time exceeds a predetermined value, the controller 69 determines in step S10 that it is time to perform adjustment of the atmosphere release valve 65. In this case, the controller 69 may also determine that it is time to perform adjustment of the atmosphere release valve 65 when the elapsed time period from the stored date and time exceeds the predetermined value, and the first air feeding processing for that day is not yet performed.

For example, the memory 69a stores the date and time at which the adjustment of the atmosphere release valve 65 is performed in the past. When an operation time period of the compressor 70 from the stored date and time exceeds a predetermined value, the controller 69 determines in step S10 that it is time to perform adjustment of the atmosphere release valve 65.

For example, the controller 69 may determine in step S10 whether it is time to perform adjustment of the atmosphere release valve 65 based on the presence or absence of instructions from a user via the operation portion 7.

In step S30, the controller 69 determines whether it is time to perform the air feeding processing of feeding air into the endoscope conduit 120.

When the controller 69 determines in step S30 that it is time to perform the air feeding processing, the processing advances to step S40 in which the air feeding processing is performed and, thereafter, the processing shown in FIG. 2 is finished. When the controller 69 determines in step S30 that it is not time to perform the air feeding processing, step S40 is skipped, and the processing shown in FIG. 2 is finished.

In the present embodiment, the time at which the air feeding processing is performed is predetermined to a time within the period during which the endoscope reprocessor 1 performs the reprocessing on the endoscope 100. The time at which the air feeding processing in the reprocessing is performed by the endoscope reprocessor 1 is substantially equivalent to the time at which air feeding processing is performed in a conventional technique and hence, detailed description will be omitted.

FIG. 3 is a flowchart of processing of adjusting the atmosphere release valve 65. When the processing of adjusting the atmosphere release valve 65 is performed, the endoscope conduit 120 may be connected to the endoscope connection portion 61, or may not be connected to the endoscope connection portion 61.

In the processing of adjusting the atmosphere release valve 65 in step S20, first, the controller 69 brings the opening and closing valve 64 into a closed state in step S100. Next, in step S110, the controller 69 starts the operation of the compressor 70 to start introduction of a gas from the compressor 70 into the first section 63c of the air feeding conduit 63. In step S120, the controller 69 starts detection of the internal pressure in the first section 63c of the air feeding conduit 63 based on an output from the sensor 66. Step S100, step S110, and step S120 may be performed in different order, or may be performed simultaneously.

Next, in step S130, the controller 69 adjusts the atmosphere release rate of the atmosphere release valve 65 such that the internal pressure in the first section 63c of the air feeding conduit 63 falls within a predetermined reference range.

The predetermined reference range is a range of air pressure suitable for a gas to be fed into the endoscope conduit 120 in the reprocessing. The predetermined reference range is set to be a minimum air pressure P min or more and a maximum air pressure P max or less. The minimum air pressure P min of the reference range is higher than air pressure required for a gas to be fed into the endoscope conduit 120 in the reprocessing. The maximum air pressure P max of the reference range is lower than the upper limit of air pressure allowed in the endoscope conduit 120, and is lower than the maximum air pressure of gas ejected from the compressor 70 according to the specifications.

Specifically, in step S130, when the internal pressure in the first section 63c is higher than the maximum air pressure P max of the reference range, the controller 69 increases the atmosphere release rate of the atmosphere release valve 65. In the present embodiment, when the internal pressure in the first section 63c is higher than the maximum air pressure P max of the reference range, the controller 69 increases the cross-sectional area of the flow passage between the input port 65a and the output port 65b of the atmosphere release valve 65.

When the internal pressure in the first section 63c is lower than the minimum air pressure P min of the reference range, the controller 69 reduces the atmosphere release rate of the atmosphere release valve 65. In the present embodiment, when the internal pressure in the first section 63c is lower than the minimum air pressure P min of the reference range, the controller 69 reduces the cross-sectional area of the flow passage between the input port 65a and the output port 65b of the atmosphere release valve 65.

Next, in step S140, the controller 69 causes the memory 69a to store the adjustment state of the atmosphere release valve 65 in which the internal pressure in the first section 63c falls within the reference range. In the case where the adjustment state of the atmosphere release valve 65 is already stored in the memory 69a at the time of performing step S140, the information is rewritten to a new adjustment state. The controller 69 may be configured to continue maintaining the adjustment state of the atmosphere release valve 65 in step S130 without storing the adjustment state of the atmosphere release valve 65.

Then, in step S150, the controller 69 stops the operation of the compressor 70 to stop introduction of a gas from the compressor 70 into the first section 63c of the air feeding conduit 63. After step S150 is performed, the controller 69 finishes the processing of adjusting the atmosphere release valve 65, and the processing returns to the flowchart shown in FIG. 2.

Although not shown in the drawing, in the case where the internal pressure in the first section 63c does not fall within the reference range even when the atmosphere release rate of the atmosphere release valve 65 is adjusted in step S130, the controller 69 notifies a user of occurrence of abnormality via the display unit 8.

In the above-described processing of adjusting the atmosphere release valve, as shown in step S100, step S110, and step S120, the controller 69 performs step I in which a gas is introduced from the compressor 70 into the air feeding conduit 63 in a state where the opening and closing valve 64 is closed, and the internal pressure in the air feeding conduit 63 is detected by the sensor 66. In the processing of adjusting the atmosphere release valve, as shown in step S130, the controller 69 performs step II in which the atmosphere release rate of a gas from the atmosphere release valve 65 is adjusted such that the internal pressure in the air feeding conduit 63 falls within the predetermined reference range.

FIG. 4 is a flowchart of the air feeding processing. Before the air feeding processing is performed, the endoscope conduit 120 is connected to the endoscope connection portion 61 with an operation performed by the user. In other words, after step II is performed, step II' is performed in which the endoscope conduit 120 is connected to the endoscope connection portion 61.

In the air feeding processing in step S40, first, the controller 69 brings the opening and closing valve 64 into a closed state in step S300. Next, in step S310, the controller 69 reads the adjustment state of the atmosphere release valve 65, which is stored in the memory 69a, and the controller 69 brings the atmosphere release valve 65 into the adjustment state which is read. In the case where the controller 69 continues maintaining the adjustment state of the atmosphere release valve 65 without changing the adjustment state after step S130 is performed, step S310 can be skipped.

Next, in step S320, the controller 69 starts the operation of the compressor 70 to start introduction of a gas from the compressor 70 into the first section 63c of the air feeding conduit 63. Step S300, step S310, and step S320 may be performed in different order, or may be performed simultaneously.

Next, in step S330, the controller 69 waits for a predetermined time period. In step S330 in which the controller 69 waits, the internal pressure in the first section 63c of the air feeding conduit 63 is changed to fall within the reference range. Note that in step S330, the controller 69 may finish waiting after the sensor 66 confirms that the internal pressure in the first section 63c is changed to fall within the reference range.

Next, in step S340, the controller 69 brings the opening and closing valve 64 into an open state. The opening and closing valve 64 is brought into an open state and hence, a gas in the first section 63c of the air feeding conduit 63 is discharged from the endoscope connection portion 61. In other words, by performing step S340, sending of a gas from the air feeding device 60 into the endoscope conduit 120 is started. At the time of performing step S340, the compressor 70 is in an operation state, and introduction of a gas from the compressor 70 into the first section 63c of the air feeding conduit 63 is continued.

Next, in step S350, the controller 69 waits for a predetermined time period. The waiting time period in step S350 is a time period during which feeding of a gas into the endoscope conduit 120 is continued in the reprocessing.

Next, in step S360, the controller 69 brings the opening and closing valve 64 into a closed state. By performing step S360, sending of a gas from the air feeding device 60 into the endoscope conduit 120 is stopped.

Next, in step S370, the controller 69 stops the operation of the compressor 70 to stop introduction of a gas from the compressor 70 into the air feeding conduit 63. After step S370 is performed, the controller 69 finishes the air feeding processing, and the processing returns to the flowchart shown in FIG. 2. After step S350 is performed, step S360 may be skipped and step S370 be performed to stop sending of a gas from the air feeding device 60 into the endoscope conduit 120.

In the above-described air feeding processing, as shown in step S300, step S310, and step S320, the controller 69 performs step III in which the atmosphere release valve 65 is maintained in the adjustment state stored in step II, the opening and closing valve 64 is closed, and a gas is introduced from the compressor 70 into the air feeding conduit 63. In the air feeding processing, as shown in step S330 and step S340, the controller 69 performs step IV in which, in a state where a gas is introduced from the compressor 70 into the air feeding conduit 63 and the internal pressure in the air feeding conduit 63 falls within the predetermined reference range, the opening and closing valve 64 is opened so as to discharge a gas in the air feeding conduit 63 from the endoscope connection portion 61.

In the above-described air feeding device 60 and method for controlling the air feeding device 60 of the present embodiment, steps I and II (step S100 to step S140) are performed and, thereafter, step III (step S300 to step S320) is performed. Therefore, even in the case where pressure of a gas ejected from the compressor 70 fluctuates, it is possible to cause the internal pressure in the first section 63c of the air feeding conduit 63 to fall within the predetermined reference range. In the air feeding device 60 and the method for controlling the air feeding device 60 of the present embodiment, step III is performed and, thereafter, step IV (step S330 and step S340) is performed. Therefore, it is possible to feed a gas in the first section 63c with an air pressure which falls within the predetermined reference range into the endoscope conduit 120.

As described above, according to the air feeding device 60 and the method for controlling the air feeding device 60 of the present embodiment, it is possible to feed a gas ejected from the compressor 70 into the endoscope conduit 120 at a pressure which falls within a predetermined range.

Second Embodiment

Hereinafter, a second embodiment of the present invention will be described. Hereinafter, only points which make the second embodiment different from the first embodiment will be described. Constituent elements substantially equivalent to the corresponding constituent elements in the first embodiment are given the same reference symbols, and the description of such constituent elements will be omitted when appropriate.

Figure 5:
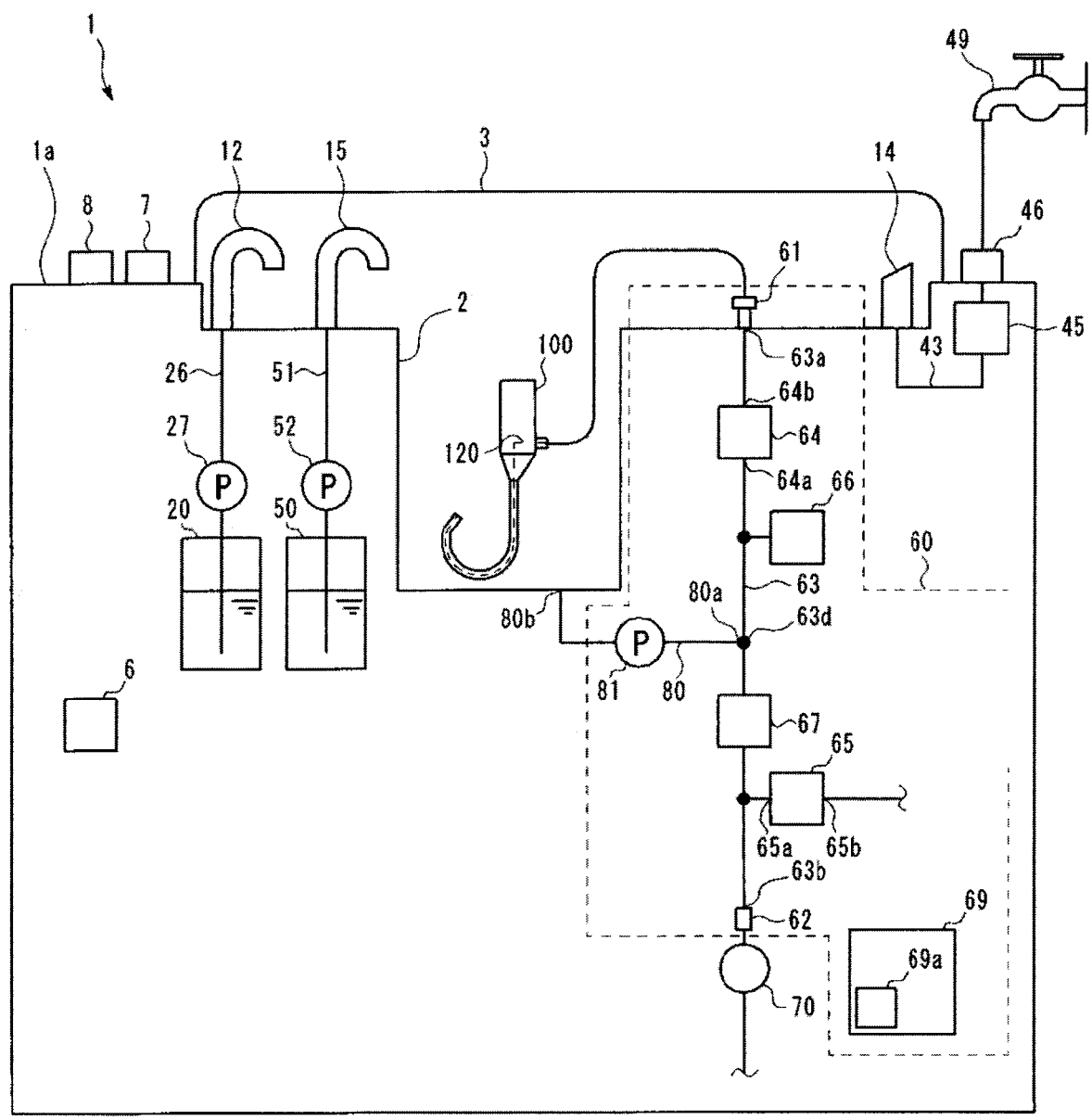
FIG. 5 is a view showing configurations of an endoscope reprocessor and an air feeding device of a second embodiment.

The air feeding device 60 of the present embodiment shown in FIG. 5 includes a liquid feeding conduit 80, a liquid introduction unit 81, and a check valve 67.

The liquid feeding conduit 80 and the liquid introduction unit 81 introduce liquid into a section of the air feeding conduit 63 which is disposed between the opening and closing valve 64 and the atmosphere release valve 65. The liquid feeding conduit 80 is connected to the section of the air feeding conduit 63 which is disposed between the opening and closing valve 64 and the atmosphere release valve 65. The liquid introduction unit 81 introduces liquid into the liquid feeding conduit 80.

The kind of liquid introduced into the liquid feeding conduit 80 by the liquid introduction unit 81 is not particularly limited. The liquid introduced into the liquid feeding conduit 80 by the liquid introduction unit 81 may be water, cleaning solution, disinfecting liquid, or alcohol.

In the present embodiment, for example, the liquid introduction unit 81 introduces liquid stored in the treatment tank 2 into the liquid feeding conduit 80. As described above, the endoscope reprocessor 1 has a configuration of introducing water, cleaning solution, or disinfecting liquid, being liquid, into the treatment tank 2.

More specifically, one end 80a, being a first end of the liquid feeding conduit 80, is connected to the section of the air feeding conduit 63 which is disposed between the opening and closing valve 64 and the atmosphere release valve 65. The other end 80b, being a second end of the liquid feeding conduit 80, is connected to the treatment tank 2. The liquid introduction unit 81 includes a pump provided to the liquid feeding conduit 80.

The liquid introduction unit 81 is electrically connected to the controller 69, and the action of the liquid introduction unit 81 is controlled by the controller 69. When the liquid introduction unit 81 is driven, liquid in the treatment tank 2 is introduced into the air feeding conduit 63 via the liquid feeding conduit 80. Note that a mode may be adopted where the liquid introduction unit 81 introduces liquid stored in a container different from the treatment tank into the air feeding conduit 63.

The check valve 67 is disposed in a section of the air feeding conduit 63 which is disposed between a connection portion 63d with the liquid feeding conduit 80 and the atmosphere release valve 65. The check valve 67 allows the flow of fluid in the air feeding conduit 63 in a direction from the atmosphere release valve 65 toward the connection portion 63d with the liquid feeding conduit 80, but restricts the flow of fluid in a direction opposite to the direction from the atmosphere release valve 65 toward the connection portion 63d.

The check valve 67 prevents liquid, introduced into the air feeding conduit 63 via the liquid feeding conduit 80, from flowing into the atmosphere release valve 65 and the compressor connection portion 62. In other words, the check valve 67 is provided and hence, liquid introduced into the air feeding conduit 63 via the liquid feeding conduit 80 flows into the endoscope connection portion 61 when the opening and closing valve 64 is in an open state.

Figure 6:
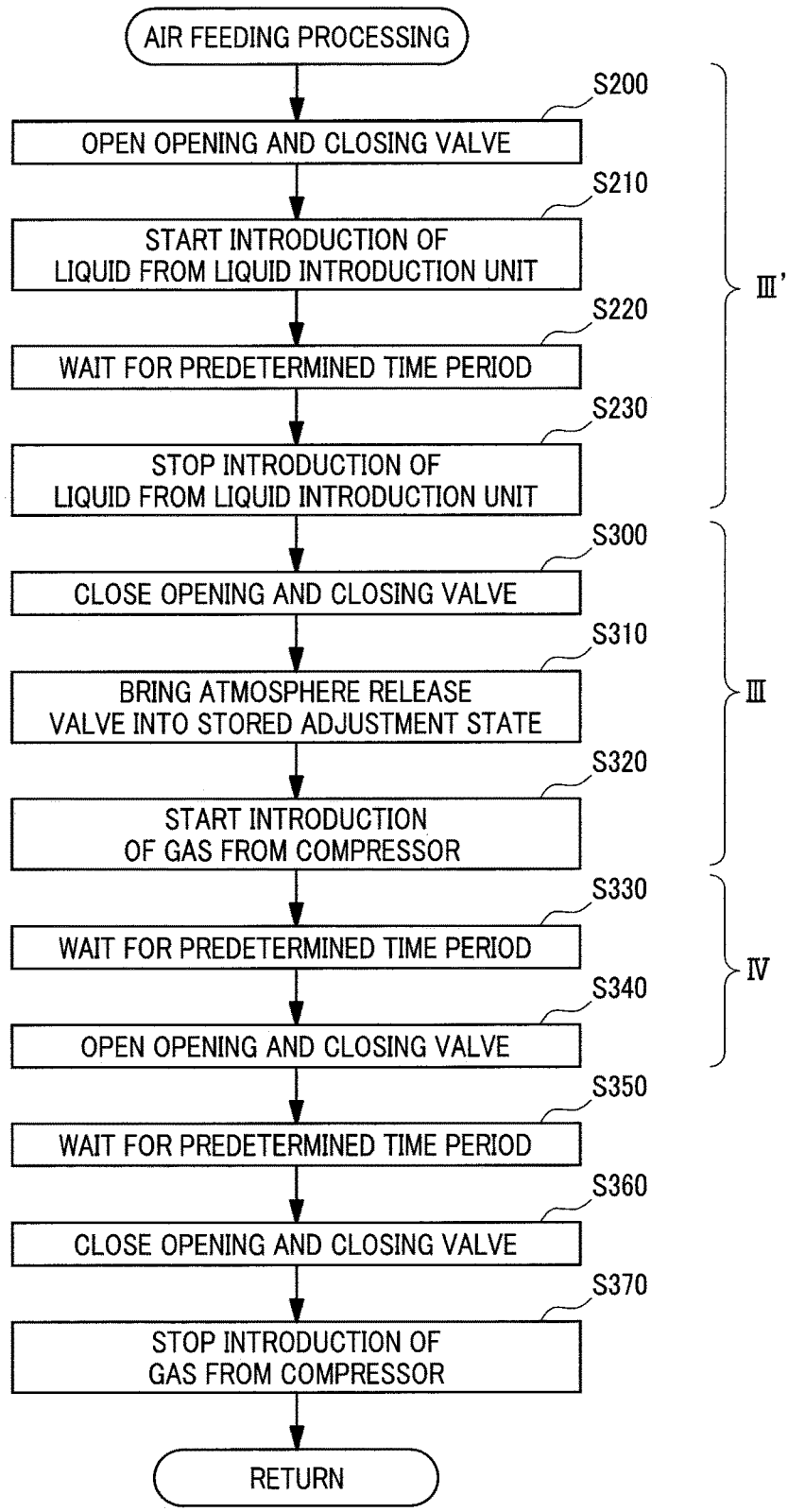
FIG. 6 is a flowchart of air feeding processing in the second embodiment.

The action of the controller 69 in the present embodiment differs from the corresponding action in the first embodiment with respect to air feeding processing. FIG. 6 is a flowchart of the air feeding processing in the present embodiment. The air feeding processing in the present embodiment shown in FIG. 6 differs from the air feeding processing in the first embodiment with respect to a point that step S200 to S230 are performed before step S300 is performed.

In the same manner as the first embodiment, before the air feeding processing is performed, step II', in which the endoscope conduit 120 is connected to the endoscope connection portion 61, is performed with an operation performed by the user.

In the air feeding processing in the present embodiment, first, the controller 69 brings the opening and closing valve 64 into an open state in step S200. Next, in step S210, the controller 69 starts the drive of the liquid introduction unit 81 to start introduction of liquid into the air feeding conduit 63. Note that at the time of performing step S210, liquid is stored in the treatment tank 2.

By performing step S210, liquid in the treatment tank 2 is introduced into the endoscope conduit 120 via the liquid feeding conduit 80, the air feeding conduit 63, and the endoscope connection portion 61. Next, in step S220, the controller 69 waits for a predetermined time period. In step S220 in which the controller 69 waits, the inside of the endoscope conduit 120 is filled with liquid. Next, in step S230, the controller 69 stops the drive of the liquid introduction unit 81 to stop introduction of liquid into the air feeding conduit 63.

After step S230 is performed, the controller 69 performs step S300 and the following steps in the same manner as the first embodiment.

In the above-described air feeding processing in the present embodiment, as shown in step S200 to step S230, the controller 69 performs step III', in which the opening and closing valve 64 is released, and the liquid introduction unit 81 is driven to fill the inside of the endoscope conduit 120 with liquid, before the controller 69 performs step III.

In the above-described air feeding device 60 and method for controlling the air feeding device 60 of the present embodiment, a gas in the first section 63c with an air pressure which falls within a predetermined reference range is fed into the endoscope conduit 120 in a state where the inside of the endoscope conduit 120 is filled with liquid. Therefore, it is possible to generate a multi-phase flow (gas-liquid two-phase flow), where liquid and a gas are mixed, in the endoscope conduit 120.

The gas-liquid two-phase flow is highly effective in detaching substances adhering to a wall surface compared with the case where only a gas or only a liquid is caused to flow through the endoscope conduit 120. Accordingly, the endoscope reprocessor 1 including the air feeding device 60 of the present embodiment can exhibit high cleaning power in the endoscope conduit 120.

Third Embodiment

Hereinafter, a third embodiment of the present invention will be described. Hereinafter, only points which make the third embodiment different from the first embodiment will be described. Constituent elements substantially equivalent to the corresponding constituent elements in the first embodiment are given the same reference symbols, and the description of such constituent elements will be omitted when appropriate.

Figure 7:
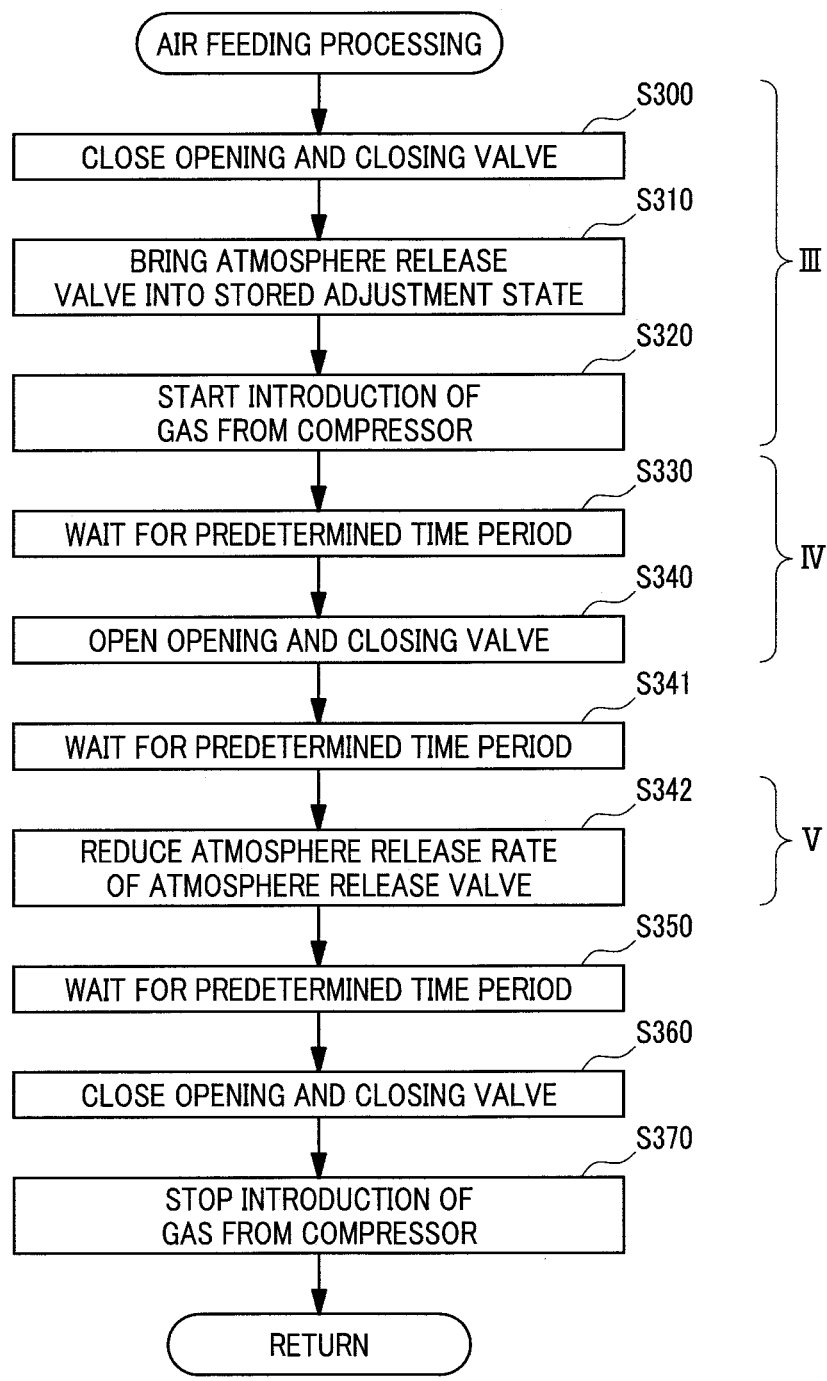
FIG. 7 is a flowchart of air feeding processing in a third embodiment.

The air feeding device 60 and the method for controlling the air feeding device 60 of the present embodiment differ from the air feeding device 60 and the method for controlling the air feeding device 60 of the first embodiment with respect to air feeding processing. FIG. 7 is a flowchart of the air feeding processing in the present embodiment. The air feeding processing in the present embodiment shown in FIG. 7 differs from the air feeding processing in the first embodiment with respect to a point that step S341 and step S342 are performed between step S340 and step S350.

In the air feeding processing in the present embodiment, first, the controller 69 brings the opening and closing valve 64 into a closed state in step S300. Next, in step S310, the controller 69 reads the adjustment state of the atmosphere release valve 65 which is stored in the memory 69a, and the controller 69 brings the atmosphere release valve 65 into the adjustment state which is read.

Next, in step S320, the controller 69 starts the operation of the compressor 70 to start introduction of a gas from the compressor 70 into the first section 63c of the air feeding conduit 63. Step S300, step S310, and step S320 may be performed in different order, or may be performed simultaneously.

Next, in step S330, the controller 69 waits for a predetermined time period. In step S330 in which the controller 69 waits, the internal pressure in the first section 63c of the air feeding conduit 63 is changed to fall within the reference range. In step S330, the controller 69 may finish waiting after the sensor 66 confirms that the internal pressure in the first section 63c is changed to fall within the reference range.

Next, in step S340, the controller 69 brings the opening and closing valve 64 into an open state. The opening and closing valve 64 is brought into an open state and hence, a gas in the first section 63c of the air feeding conduit 63 is discharged from the endoscope connection portion 61. In other words, by performing step S340, sending of a gas from the air feeding device 60 into the endoscope conduit 120 is started. At the time of performing step S340, the compressor 70 is in an operation state, and introduction of a gas from the compressor 70 into the first section 63c of the air feeding conduit 63 is continued.

Next, in step S341, the controller 69 waits for a predetermined time period. In step S342, the controller 69 reduces the atmosphere release rate of the atmosphere release valve 65. In step S342, the controller 69 may set the atmosphere release rate to zero by closing the atmosphere release valve 65.

Next, in step S350, the controller 69 waits for a predetermined time period. The waiting time period in step S350 is a time period during which feeding of a gas into the endoscope conduit 120 is continued in the reprocessing.

In the present embodiment, the atmosphere release rate of the atmosphere release valve 65 is reduced by performing step S342. With such reduction in the atmosphere release rate, it is possible to increase the flow speed of a gas flowing through the endoscope conduit 120 at the time of performing step S350 compared with the first embodiment.

Next, in step S370, the controller 69 stops the operation of the compressor 70 to stop introduction of a gas from the compressor 70 into the air feeding conduit 63. After step S350 is performed, step S360 may be skipped and step S370 be performed to stop sending of a gas from the air feeding device 60 into the endoscope conduit 120.

In the above-described air feeding processing in the present embodiment, after step IV is performed, as shown in step S341 and step S342, the controller 69 performs step V in which the atmosphere release rate of the atmosphere release valve 65 is reduced while introduction of a gas from the compressor 70 into the air feeding conduit 63 is maintained.

In the above-described air feeding device 60 and method for controlling the air feeding device 60 of the present embodiment, it is possible to increase the flow speed of a gas flowing through the endoscope conduit 120 compared with the first embodiment and hence, it is possible to rapidly remove droplets or the like in the endoscope conduit 120.

Step S341 and step S342 in the present embodiment may be performed after step S340 of the air feeding processing shown in FIG. 6 in the second embodiment. When step S341 and step S342 in the present embodiment are performed in the air feeding processing in the second embodiment, it is possible to increase the flow speed of a gas-liquid two-phase flow in the endoscope conduit 120 and hence, higher cleaning power can be obtained.

Fourth Embodiment

Hereinafter, a fourth embodiment of the present invention will be described. Hereinafter, only points which make the fourth embodiment different from the second embodiment will be described. Constituent elements substantially equivalent to the corresponding constituent elements in the second embodiment are given the same reference symbols, and the description of such constituent elements will be omitted when appropriate.

Figure 8:
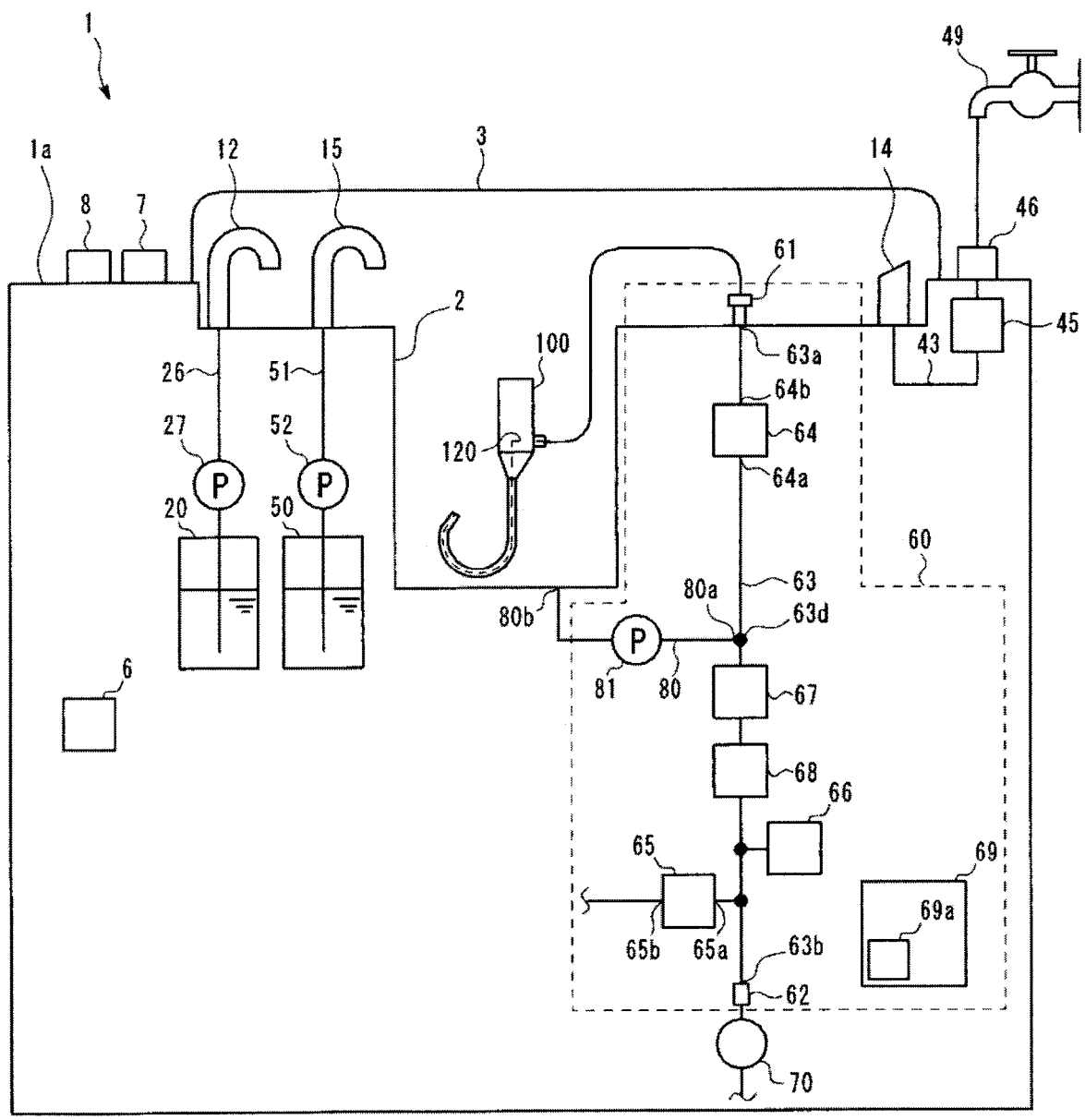
FIG. 8 is a view showing configurations of an endoscope reprocessor and an air feeding device of a fourth embodiment.

The air feeding device 60 of the present embodiment shown in FIG. 8 includes a second opening and closing valve 68. The second opening and closing valve 68 is disposed in a section of the air feeding conduit 63 which is disposed between the check valve 67 and the atmosphere release valve 65. The second opening and closing valve 68 is electrically connected to the controller 69, and the action of the second opening and closing valve 68 is controlled by the controller 69. The sensor 66 in the present embodiment is disposed in a section of the air feeding conduit 63 which is disposed between the second opening and closing valve 68 and the other end 63b.

In the air feeding processing shown in FIG. 6, the air feeding device 60 of the present embodiment can start the steps shown in step S310 to step S330 by closing the second opening and closing valve 68 instead of closing the opening and closing valve 64, during the period in which step III' shown in step S200 to step S230 is performed to fill the inside of the endoscope conduit 120 with liquid. In this case, the opening and closing valve 64 and the second opening and closing valve 68 are opened in S340. With such a configuration, the air feeding device 60 of the present embodiment can perform the air feeding processing in a shorter time period.

Fifth Embodiment

Hereinafter, a fifth embodiment of the present invention will be described. Hereinafter, only points which make the fifth embodiment different from the first embodiment will be described. Constituent elements substantially equivalent to the corresponding constituent elements in the first embodiment are given the same reference symbols, and the description of such constituent elements will be omitted when appropriate.

The first embodiment adopts a mode where the compressor 70 is included in the endoscope reprocessor 1, and the action of the compressor 70 is controlled by the controller 69. However, the compressor 70 may be disposed outside the endoscope reprocessor 1.

Figure 9:
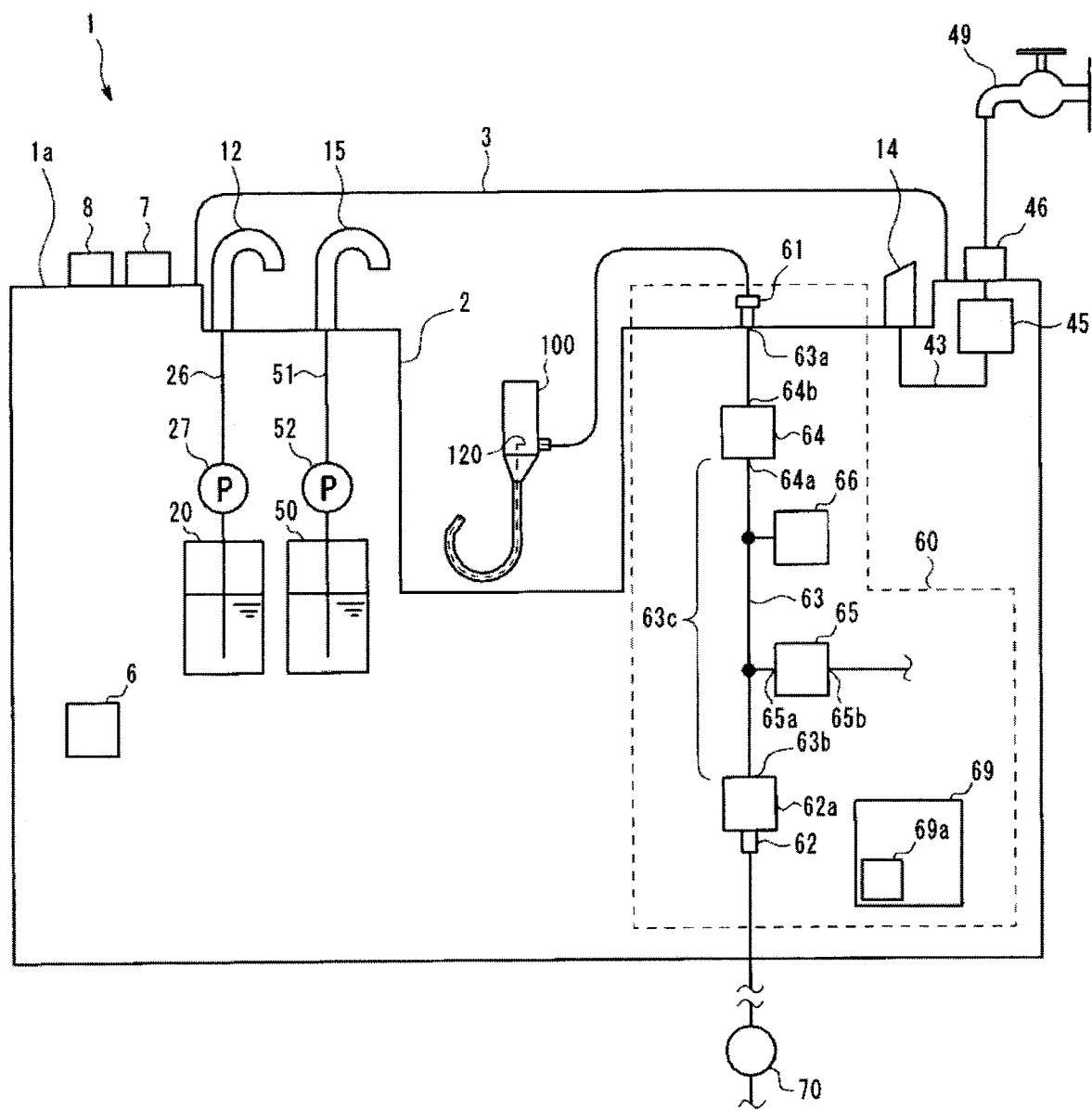
FIG. 9 is a view showing configurations of an endoscope reprocessor and an air feeding device of a fifth embodiment.

In the endoscope reprocessor 1 of the present embodiment shown in FIG. 9, the compressor 70 is disposed outside the endoscope reprocessor 1. The compressor 70 in the present embodiment continues to supply a gas at a predetermined pressure to the endoscope reprocessor 1.

In the air feeding device 60 of the present embodiment, the compressor connection portion 62 includes a gas supply valve 62a. The gas supply valve 62a is electrically connected to the controller 69, and the action of the gas supply valve 62a is controlled by the controller 69.

When the gas supply valve 62a is in an open state, a gas ejected from the compressor 70 is introduced into the first section 63c of the air feeding conduit 63. In other words, in the case of starting introduction of a gas from the compressor 70 into the first section 63c of the air feeding conduit 63, the controller 69 in the present embodiment switches the gas supply valve 62a from a closed state to an open state. In the case of stopping introduction of a gas from the compressor 70 into the first section 63c of the air feeding conduit 63, the controller 69 switches the gas supply valve 62a from an open state to a closed state.

Specifically, in the processing of adjusting the atmosphere release valve shown in FIG. 3, the controller 69 brings the gas supply valve 62a into an open state in step S110. The controller 69 brings the gas supply valve 62a into a closed state in step S150. In the air feeding processing shown in FIG. 4, the controller 69 brings the gas supply valve 62a into an open state in step S320. The controller 69 brings the gas supply valve 62a into a closed state in step S370.

The air feeding device 60 of the present embodiment differs from the air feeding device 60 of the first embodiment with respect to a configuration of introducing a gas from the compressor 70 into the air feeding conduit 63 and a control of the air feeding device 60, and other configurations and control in the present embodiment are substantially equivalent to the corresponding configurations and control in the first embodiment. Accordingly, in the same manner as the first embodiment, the air feeding device 60 and the method for controlling the air feeding device 60 of the present embodiment allow a gas ejected from the compressor 70 to be fed into the endoscope conduit 120 at a pressure which falls within a predetermined range.

The air feeding device 60 of the present embodiment may include the liquid feeding conduit 80, the liquid introduction unit 81, and the check valve 67 as in the case of the second embodiment. In this case, the air feeding device 60 and the method for controlling the air feeding device 60 of the present embodiment can generate a gas-liquid two-phase flow in the endoscope conduit 120.

The air feeding device 60 and the method for controlling the air feeding device 60 of the present embodiment may perform the air feeding processing shown in FIG. 7 in the third embodiment. In this case, the air feeding device 60 and the method for controlling the air feeding device 60 of the present embodiment can further increase the flow speed of a gas flowing through the endoscope conduit 120.

Sixth Embodiment

Hereinafter, a sixth embodiment of the present invention will be described. Hereinafter, only points which make the sixth embodiment different from the first embodiment will be described. Constituent elements substantially equivalent to the corresponding constituent elements in the first embodiment are given the same reference symbols, and the description of such constituent elements will be omitted when appropriate.

Figure 10:
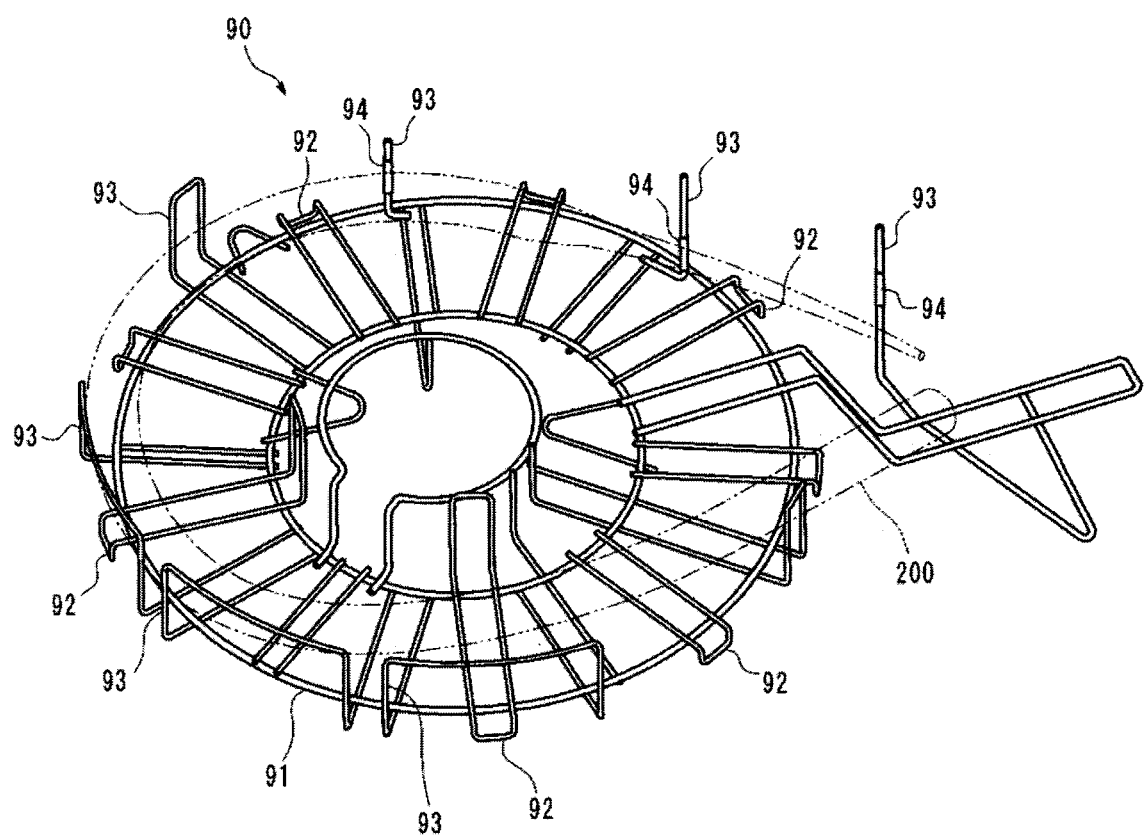
FIG. 10 is a perspective view of a holding net which is included in an endoscope reprocessor of a sixth embodiment.

FIG. 10 is a perspective view of a holding net 90 included in the endoscope reprocessor 1 of the present embodiment. The holding net 90 shown in FIG. 10 is a device which holds a tubular medical instrument 200, such as a dilator, in the treatment tank 2. FIG. 10 is a view of the holding net 90 disposed in the treatment tank 2 as viewed from an obliquely upward position.

The holding net 90 includes a body portion 91, a plurality of leg portions 92, and a plurality of restricting portions 93. The body portion 91 is a net-like portion having a substantially circular outer peripheral shape. The body portion 91 is in a substantially horizontal state in the treatment tank 2. The leg portions 92 extend downward from the body portion 91. The leg portions 92 are brought into contact with the bottom surface of the treatment tank 2, so that the body portion 91 has a separation from the bottom surface of the treatment tank 2 in the upward direction.

The plurality of restricting portions 93 are columnar members extending upward from the outer edge of the body portion 91. In other words, the plurality of restricting portions 93 are arranged on substantially the same circumference. The plurality of restricting portions 93 hold the tubular medical instrument 200 in an arc shape, the tubular medical instrument 200 being placed above the body portion

91. In FIG. 10, an outer shape of the tubular medical instrument 200 is indicated by a dashed-and-double-dotted line.

The holding net 90 in the present embodiment differs from a holding net for endoscope which holds an endoscope in the treatment tank 2 of the endoscope reprocessor 1 with respect to the arrangement of the plurality of restricting portions 93. The tubular medical instrument 200, such as a dilator, has a larger outer diameter than an insertion portion of an endoscope and the cable. To allow the holding net 90 in the present embodiment to hold the tubular medical instrument 200 having a large diameter, the holding net 90 has the smaller number of restricting portions 93 than the holding net for endoscope.

To easily distinguish the holding net 90 in the present embodiment from the holding net for endoscope, the holding net 90 includes one or a plurality of distinguishing labels 94. In the present embodiment, the distinguishing labels 94 are fixed to the outer peripheries of the restricting portions 93.

With the use of the holding net 90 in the present embodiment, the endoscope reprocessor 1 can perform reprocessing on the tubular medical instrument 200.

The present invention is not limited to the above-mentioned embodiments, and can be suitably changed without departing from the gist or concept of the invention which can be read in the claims and in the entire description. A method for controlling an air feeding device and an air feeding device with such changes also fall within a technical scope of the present invention.

What is claimed is:

1. An air feeding device comprising:
a first conduit having a first end and a second end;
a first valve disposed in the first conduit;
an atmosphere release valve connected to the first conduit at a first position between the second end and the first valve, the atmosphere release valve being configured to adjust an atmosphere release rate of a gas from the first conduit;
a sensor configured to detect an internal pressure in the first conduit; and
one or more processors comprising hardware, wherein the one or more processors are configured to:
control the first valve to close;
control a compressor to introduce the gas into the first conduit;
control the sensor to detect the internal pressure;
control the atmosphere release valve to adjust the atmosphere release rate such that the internal pressure falls within a predetermined range;
control the compressor to stop introducing the gas into the first conduit;
control the atmosphere release valve to adjust the atmosphere release valve to a state that corresponds to the atmosphere release rate such that the internal pressure falls within the predetermined range;
control the compressor to introduce the gas into the first conduit; and
control the first valve to open to allow the gas from the first conduit to flow to an endoscope connected to the first end of the first conduit.

2. The air feeding device according to claim 1, comprising:
a second conduit connected to the first conduit at a second position between the first valve and the atmosphere release valve;
a pump configured to introduce liquid into the second conduit; and
a check valve disposed in the first conduit at a third position between the second position and the atmosphere release valve,
wherein the one or more processors are configured to, before controlling the compressor to introduce the gas into the first conduit for the second time, control the first valve to open and drive the pump to introduce the liquid through the second conduit, the first conduit, and the first end of the first conduit to fill an inside of an endoscope conduit of the endoscope with the liquid.

3. The air feeding device according to claim 2, further comprising:
an endoscope connector configured to connect the endoscope conduit of the endoscope to the first end of the first conduit,
wherein the one or more processors are configured to control the first valve to open and drive the pump to introduce the liquid to fill the inside of the endoscope conduit after the endoscope conduit of the endoscope is connected to the first end of the first conduit by the endoscope connector.

4. The air feeding device according to claim 1, wherein the one or more processors are configured to, after controlling the first valve to open to allow the gas from the first conduit to flow to the endoscope connected to the first conduit, control the atmosphere release valve to reduce the atmosphere release rate while maintaining introduction of the gas from the compressor into the first conduit.

5. The air feeding device according to claim 1, wherein the gas is air.

6. The air feeding device according to claim 1, wherein:
the sensor is connected to the first conduit between the first valve and the second end; and
the sensor is configured to detect the internal pressure of the first conduit between the first valve and the second end.

7. The air feeding device according to claim 1,
wherein the one or more processors are configured to determine whether it is time to control the atmosphere release valve to adjust the atmosphere release rate.

8. The air feeding device according to claim 7,
wherein the one or more processors are configured to control the first valve to close in response to determining that it is time to control the atmosphere release valve to adjust the atmosphere release rate.

9. The air feeding device according to claim 1,
wherein the one or more processors are configured to determine whether it is time to feed air into an endoscope conduit of the endoscope.

10. The air feeding device according to claim 9,
wherein the one or more processors are configured to, in response to determining that it is time to feed air into the endoscope conduit, control the first valve to close and control the atmosphere release valve to adjust the atmosphere release valve to the state.

11. The air feeding device according to claim 1,
wherein the one or more processors are configured to, in response to controlling the atmosphere release valve to adjust the atmosphere release rate such that the internal pressure falls within the predetermined range, cause a memory to store the state.

12. The air feeding device according to claim 11,
wherein the one or more processors are configured to:
read the stored state; and
control the atmosphere release valve to adjust the atmosphere release valve to the stored state.

13. The air feeding device according to claim 1, wherein the one or more processors are configured to, subsequent to controlling the atmosphere release valve to adjust the atmosphere release rate such that the internal pressure falls within the predetermined range, control the first valve to close.

14. The air feeding device according to claim 1, further comprising:
an endoscope connector configured to connect the first end of the first conduit to an endoscope conduit of the endoscope.

15. The air feeding device according to claim 1, further comprising:
a compressor connector configured to connect the compressor to the second end of the first conduit.

16. A control device for controlling an air feeding device, the control device comprising:
one or more processors comprising hardware, wherein the one or more processors are configured to:
control a first valve, disposed between a first end and a second end of a first conduit of the air feeding device, to close;
control a compressor to introduce gas into the first conduit;
control a sensor to detect an internal pressure in the first conduit;
control a an atmosphere release valve, connected to the first conduit at a first position between the second end and the first valve, to adjust an atmosphere release rate of a gas from the first conduit, such that an internal pressure in the first conduit falls within a predetermined range;
control the compressor to stop introducing the gas into the first conduit;
control the atmosphere release valve to adjust the atmosphere release valve to a state that corresponds to the atmosphere release rate such that the internal pressure falls within the predetermined range;
control the compressor to introduce the gas into the first conduit; and
control the first valve to open to allow the gas from the first conduit to flow to an endoscope connected to the first end of the first conduit.

17. The control device according to claim 16, wherein the one or more processors are configured to, in response to controlling the atmosphere release valve to adjust the atmosphere release rate such that the internal pressure falls within the predetermined range, cause a memory to store the state as a stored state.

18. The control device according to claim 17, wherein the one or more processors are configured to:
read the stored state; and
control the atmosphere release valve to assume the stored state.

19. The control device according to claim 17, wherein the one or more processors are configured to, subsequent to controlling the atmosphere release valve to adjust the atmosphere release rate such that the internal pressure falls within the predetermined range, control the first valve to close.

* * * * *